United States Patent [19]

Uchida et al.

[11] Patent Number: 5,055,220

[45] Date of Patent: Oct. 8, 1991

[54] DICYCLOHEXYLETHYLENE DERIVATIVES

[75] Inventors: Manabu Uchida; Yasuyuki Goto, both of Ichihara; Tetsuya Ogawa, Futtsu, all of Japan

[73] Assignee: Chisso Corporation, Osaka, Japan

[21] Appl. No.: 579,327

[22] Filed: Sep. 10, 1990

[30] Foreign Application Priority Data

Oct. 13, 1989 [JP] Japan .................................. 1-265131

[51] Int. Cl.$^5$ ...................... C09K 19/52; C09K 19/30; G02F 1/13; C07C 25/13
[52] U.S. Cl. ............................ 252/299.01; 252/299.63; 570/128; 359/103
[58] Field of Search ............. 252/299.01, 299.5, 299.6, 252/299.61, 299.63; 350/350 R, 350 S; 570/128

[56] References Cited

U.S. PATENT DOCUMENTS

| | | | |
|---|---|---|---|
| 4,510,069 | 4/1985 | Eidenschink et al. | 252/299.61 |
| 4,630,896 | 12/1986 | Petrzilka et al. | 350/350 R |
| 4,797,228 | 1/1989 | Goto et al. | 252/299.63 |
| 4,820,443 | 4/1989 | Goto et al. | 252/299.63 |
| 4,853,152 | 8/1989 | Goto et al. | 252/299.63 |
| 4,871,470 | 10/1989 | Wächtler et al. | 252/299.63 |
| 4,908,152 | 3/1990 | Goto et al. | 252/299.63 |
| 4,910,350 | 3/1990 | Tanaka et al. | 570/129 |
| 4,917,819 | 4/1990 | Goto et al. | 252/299.63 |

*Primary Examiner*—John S. Maples
*Assistant Examiner*—Shean C. Wu
*Attorney, Agent, or Firm*—Wenderoth, Lind & Ponack

[57] ABSTRACT

A dicyclohexylethylene derivative is disclosed which has the formula,

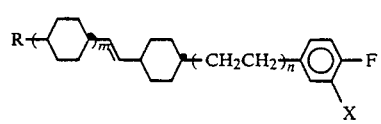

[I]

where R is a straight chain alkyl group of 1 to 8 carbon atoms, X is hydrogen or fluorine, m is 1 or 2, n is 0 or 1, and ⟩— indicates that a substituent at the 1-position of the cyclohexane ring and a substituent at the 4-position thereof are at a trans configuration. A liquid crystal composition comprises at least one of the dicyclohexylethylene derivatives of the formula [I] above.

10 Claims, No Drawings

DICYCLOHEXYLETHYLENE DERIVATIVES

BACKGROUND OF THE INVENTION

1. Field of the Invention

The present invention relates to a dicyclohexylethylene derivative, and more particularly, to a dicyclohexylethylene derivative as a liquid crystal compound suitable as a component of a display material, and a liquid crystal composition containing said derivative.

2. Description of Related Art

Liquid crystal display devices have been recently introduced, as a new display system, into personal computers, office automation machines and the like, and have gained rapidly in importance.

This is due to the fact that, among many liquid crystal display systems, a supertwisted nematic (STN) system or a supertwisted birefringence effect (SBE) system, and an active matrix system using a thin film transistor (TFT) have been recently used to meet the demand for multicolor display and large picture.

Liquid crystal materials used for these display systems are required to have various properties such as exhibiting a mesomorphic phase at temperatures where the display device is used, stability to environmental factors (moisture, heat, air, light, electricity, etc.) colorlessness, large (or small) anisotropic amount of refractive index ($\Delta n$), large (or small) elastic constant ratio, large anisotropic amount of dielectric constant ($\Delta\epsilon$), low viscosity, high specific resistance, less change of the specific resistance with time, wide d/p (d: cell thickness, p: pitch length) margin and the like.

At present, however, there is no single compound capable of sufficiently driving a display device, and therefore, practically used liquid crystal materials are liquid crystal compositions composed of a mixture of several liquid crystal compounds. Consequently, the liquid crystal compound have to be compatible with other liquid crystal compounds.

In the present specification, liquid crystal compounds mean those capable of contributing to driving liquid crystal display devices at least to some extent.

As an analogue of the compound of the present invention, a compound of the formula,

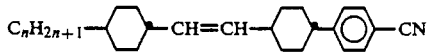

where n is 3,4,5,6 and 7 (Japanese Patent Application Laid-open No. 215336/1986) is known. However, this compound has high viscosity and less compatibility at low temperatures, and has drawbacks that the specific resistance and its change with time prevent use of the compound for TFT.

In addition, the following compounds containing fluorine atoms in the molecule are known as analogues of the compound of the present invention.

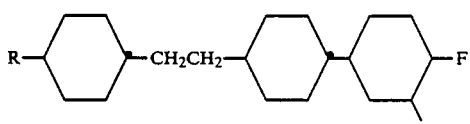

(USP 4,820,443)

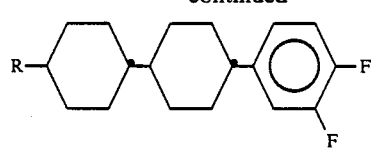

(USP 4,405,488)

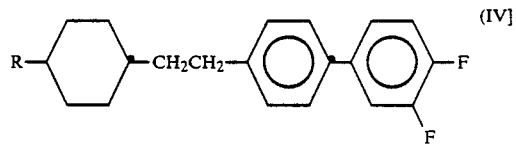

(USP 4,797,228)

In various liquid display systems as well as the above-mentioned liquid display system, wide operation range, rapid response speed, low driving voltage and the like are in demand.

SUMMARY OF THE INVENTION

An object of the present invention is to provide a liquid crystal compound exhibiting, at least partly, a wide operation range of mesomorphic phase, low viscosity, large $\Delta\epsilon$ and high stability.

Another object of the present invention is to provide a liquid crystal composition comprising the above-mentioned liquid crystal compound.

According to one aspect of the present invention, there is provided a dicyclohexylethylene derivative of the formula,

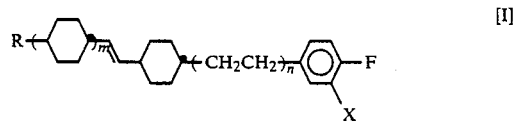

where R is a straight chain alkyl having 1-8 carbon atoms, X is a hydrogen or fluorine atom, m is 1 or 2, n is 0 or 1, and indicates that a substituent at the of 1-position of cyclohexane ring and a substituent at the 4-position thereof are at a trans configuration.

According to another aspect of the present invention, there is provided a liquid crystal composition containing at least one of the compounds of the formula (I) above.

DESCRIPTION OF THE PREFERRED EMBODIMENTS

Preferable compounds of formula [I] above include:

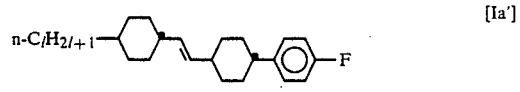

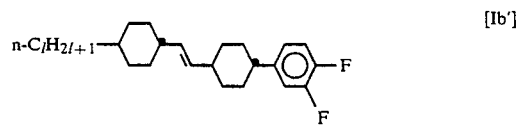

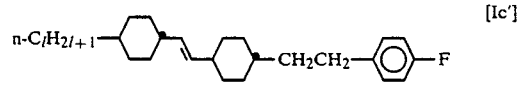

-continued

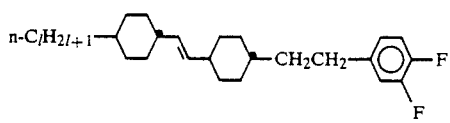 [Id']

were l is 2-7.

It has been found that these compounds have a wide mesomorphic range from about room temperature to one hundred and several tens degrees C, extremely low viscosity for three-ring compounds, and a positive $\Delta\epsilon$ value, and therefore, these compounds have turned out to be suitable for liquid crystal display devices.

Among these compounds, particularly preferable compounds are:

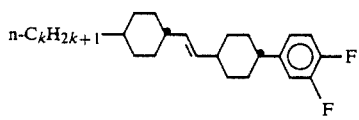 [Iba]

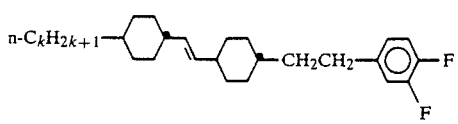 [Ida]

where k is 2-5.

Since the compounds of formula [Ib'] and [Id'] have a large positive $\Delta\epsilon$ value, the liquid crystal display devices can be driven by a low voltage. Further, the compounds of formulas [Iba] and [Iba] hardly exhibit a smectic phase and therefore, are suitable for a liquid crystal display device using a nematic phase. For example, a compound of formula [Iba] where k is 5 does not exhibit a smectic phase.

In the compounds of formula [I], the following compounds are also preferable.

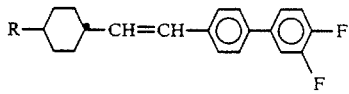 [Ie']

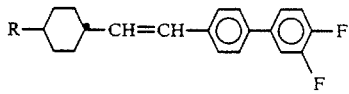 [If']

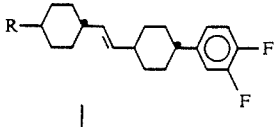 [Ig']

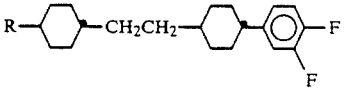 [Ih']

where j is 1-5.

In the compounds of formula [I] where m is 2, compounds of formulas [Ie'], [If'], [Ig'] and [Ih'] have very high clearing points so that the upper limit of the driving temperature range of liquid crystal display devices can be raised, and therefore, these compounds are useful.

Among these compounds, particularly preferable compounds are those of formulas of [Ie'] and [Ig'], and these compounds have large positive $\Delta\epsilon$ values so that the liquid crystal display devices can be driven by a low voltage.

Furthermore, the compounds of formula [I] have a high compatibility with other liquid crystal compounds, for example, known liquid crystal compounds such as ester type, Schiff type, ethane type, acetylene type, azoxy type, biphenyl type, cyclohexane type, cyclohexene type, pyridine type, pyrimidine type, dioxane type, fluorine type liquid crystal compounds and the like, and therefore, the compound of formula [I] can be mixed with one or more of these compounds to form liquid crystal materials suitable for various usages. Further, the liquid crystal materials are very stable to environmental factors (moisture, heat, air, light, electricity, etc.). It is clear that the present compounds are excellent, taking into consideration that a compound of the formula,

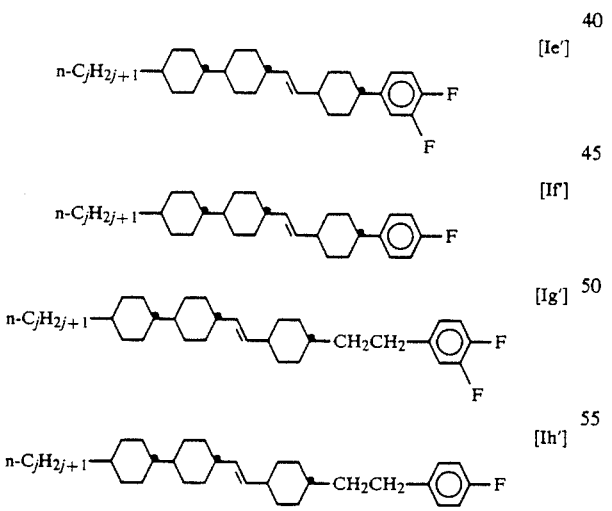

where R is as defined above, similar to the compounds of the present invention, is not stable to environmental factors.

The compound of formula [I] is also suitable for a starting material for preparing other liquid crystal compounds, for example, a liquid crystal compound of formula [II] can be prepared by the process of the following reaction formulas.

[Ib]

H$_2$, metal catalyst

[II]

The compound of the present invention may be produced by the following method:

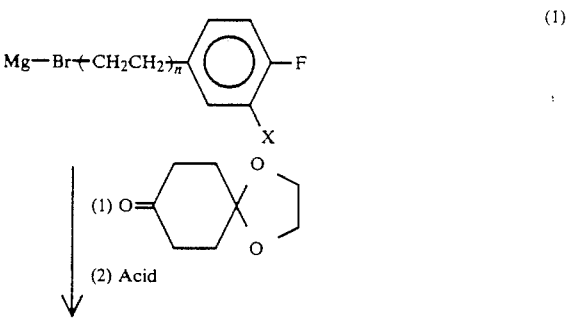 (1)

-continued

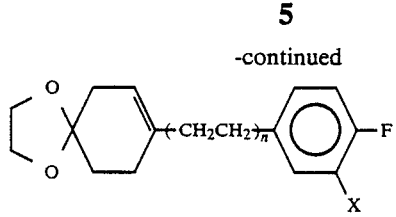   (2)

(1) H₂, metal catalyst
(2) Acid

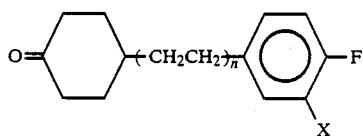   (3)

(1) CH₃OCH = P Ph₃  (a)
(2) Acid

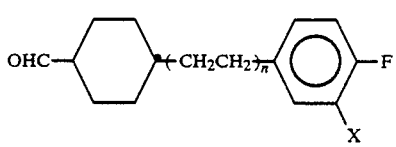   (4)

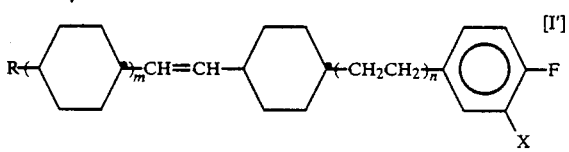

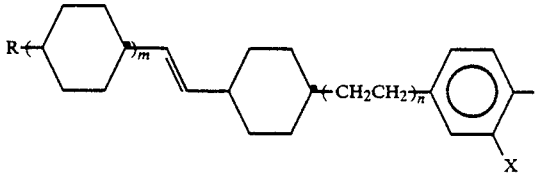   [I']

(cis/trans ≈ 95/5)

(1) Peroxide
(2) Ph₃PBr₂
(3) Zn

[I]

where R, X, m and n are as defined above.

That is, 1,4-cyclohexanedione-mono-ethyleneketal is reacted with a Grignard reagent (1) prepared from the corresponding bromide (substituted bromobenzene or substituted phenethyl bromide) followed by dehydrating with an acid catalyst (for example, p-toluenesulfonic acid, potassium hydrogen sulfate, hydrochloric acid, and sulfuric acid) to produce a cyclohexene derivative (2). The resulting cyclohexene derivative is hydrogenated in the presence of Pd, Ni, or Pt type catalyst and then treated with an aqueous acidic solution to give a cyclohexanone derivative (3).

The resulting compound (3) is reacted with an ylide of the formula (a) prepared by treating methoxymethyl triphenyl phosphonium chloride of the formula,

with a base such as n-butyl lithium, potassium t-butoxide and the like, and then treated in an acidic aqueous solution to give an aldehyde derivative (4).

The derivative (4) is treated with an ylide of the formula (b) prepared by treating a phosphonium salt (5) of the formula,

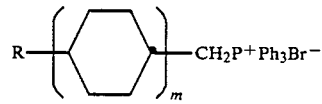

with a base such as n-butyl lithium, potassium t-butoxide to obtain a dicyclohexylethylene derivative [I∝]. This [I'] is a mixture of cis-form and trans-form and the ratio of cis:trans is about 95:5. This cis-form is converted to the trans-form to obtain the compound [I] of the present invention. That is, the ethylene derivatives [I'] are oxidized with a peroxide such as m-chloroperbenzoic acid, brominated with dibromotriphenyl phosporane and finally reduced with Zn to give the compound of the present invention, the dicyclohexylethylene derivative [I].

A feature of the liquid crystal composition of the present invention is that it contains at least two liquid crystal compounds and at lest one of them is the liquid crystal compound of formula [I] above.

Exemplary suitable liquid crystal compounds which are used together with the compound of formula [I] as components of the liquid crystal composition include the following group of known compounds (i)–(xxxiii).

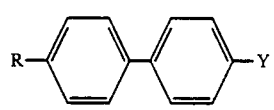  (i)

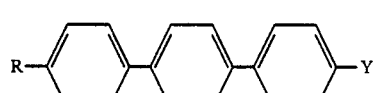  (ii)

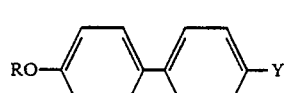  (iii)

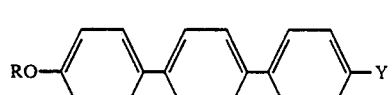  (iv)

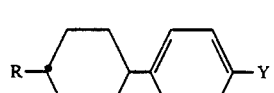  (v)

  (vi)

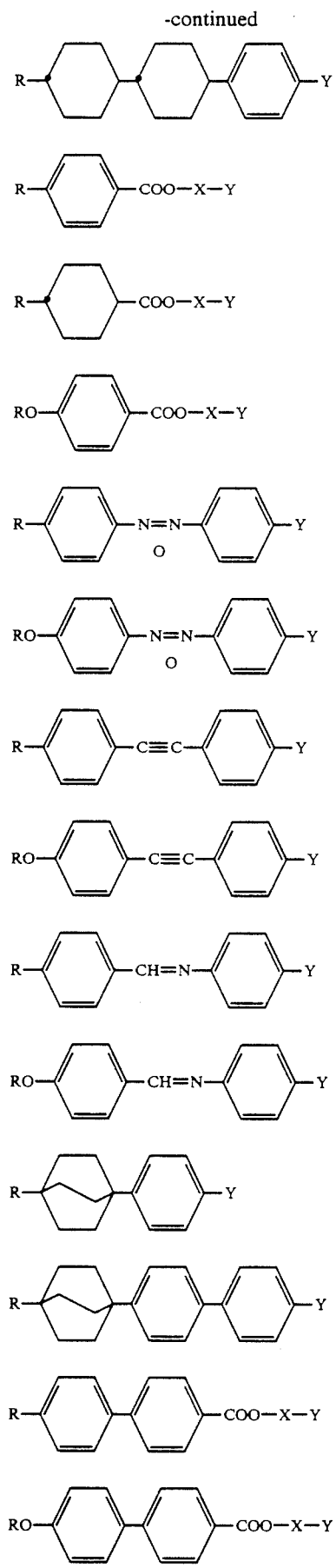

-continued

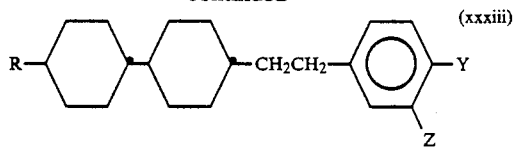

In formulas (i)-(xxxiii), X is

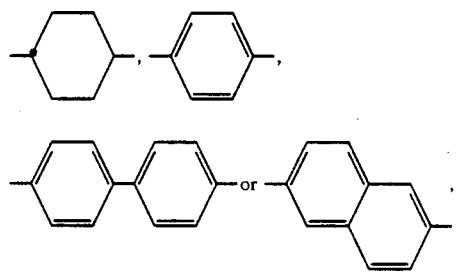

Y is —CN, —F, —CF$_3$, —OCF$_3$, R$_1$ or OR$_1$ where R and R$_1$ are independently alkyl or alkenyl, and z is —H or —F.

The NI point of the compound of the present invention is so high that the operation range of liquid crystal display devices can be broadened; its viscosity is very low and therefore the response time of liquid crystal display devices can be shortened; and further, due to its large positive Δε value, it is not required to raise the driving voltage of liquid crystal display devices.

In addition, the compound of the present invention is very stable to environmental factors and therefore, can be used for various liquid crystal display devices (for example, active matrix system by TFT).

The following examples are given for illustrating, but not limiting the present invention.

Explanation of symbols in the examples:
CN point ... Crystalline-nematic phase transition point
CS point ... Crystalline-smectic phase transition point
SN point ... Smectic-nematic phase transition point
NI point ... Nematic phase-isotropic liquid phase transition point

EXAMPLE 1

Preparation of trans-2-(trans-4-(3,4-difluorophenyl)cyclohexyl)-1-(trans-4-n-pentylcyclohexyl)ethene (l=5 in formula [Ib'] (No. 1)

(i) Preparation of 3',4'-difluorophenyl-cyclohexene-4-one-ethyleneketal (X=F, n=0 in formula (2))

To a 2 l. three-necked flask containing 8.0 g. of magnesium and 30 ml. of THF was dropwise added in a nitrogen atmosphere 250 ml. of a THF solution of 3,4-difluorobromobenzene (63.7 g.) kept at 50° C., followed by stirring for 1 hour and dropwise adding thereto 200 ml. of a THF solution of 1,4-cyclohexanedione-monoethylene ketal (46.9 g.) kept at 40° C. Continuing stirring for 10 hours as it is, 500 ml. of a saturated aqueous solution of ammonium chloride under cooling with ice and further, 500 ml. of toluene were added thereto to effect extraction. The organic layer was washed with 500 ml. of water three times, dried over sodium sulfate and concentrated.

To the product were added 0.6 g. of p-toluene-sulfonic acid and 200 ml. of toluene and refluxed for 3 hours while water in the form of azeotrope was withdrawn using a Dean Stark trap.

After cooling the product to 30° C., 200 ml. of a 0.1 N aqueous sodium hydroxide and 200 ml. of heptane were added thereto and the water layer was removed.

Then, the product was washed with 200 ml. of water three times, dried over sodium sulfate and concentrated to obtain 81.7 g. of a crude product, which was recrystallized from heptane to obtain 55.7 g. of the end product. Its structure was confirmed by NMR.

(ii) Preparation of 4-(3,4-difluorophenyl)cyclohexanone
(X =F, n=0 in formula (3))

A 300 ml. egg plant type flask containing 8.4 g. of 5% palladium carbon, 55.7 g. of the compound obtained in (i) above and 200 ml. of ethyl acetate was swept with hydrogen. Stirring was effected at 25° C. for 8 hours to consume 5 l. of hydrogen. After removing the catalyst, the resultant product was concentrated and recrystallized from alcohol to obtain 52.3 g. of a white crystal.

The crystal was dissolved in 600 ml THF, and 165 ml of 2 N hydrochloric acid was added thereto and refluxed for one hour. After allowing to cool, 300 ml. of toluene was added thereto for extraction and the extract was washed with 300 ml. of a 0.5 N aqueous sodium hydroxide and with 300 ml. of water three times, followed by drying over sodium sulfate and concentrating to obtain 40.3 g. of a crude product. The crude product was recrystallized from alcohol and dried to give 24.0 g. of the title compound, m.p. 61° C. The structure was confirmed by NMR.

(iii) Preparation of trans-4-(3,4-difluorophenyl)cyclohexane carboxyaldehyde (X=F, n=0 in formula (4))

A 1 l. three-necked flask containing 57.2 g. of methoxymethyltriphenyl phosphonium chloride and 150 ml. of THF was cooled to −10° C. and 18.7 g. of potassium tbutoxide was added thereto. After stirring the resulting mixture at 0° C. for one hour 100 ml. of a solution of the compound obtained in (ii) above (23.4 g.) in THF was dropwise added thereto, and stirring was effected for 4 hours and 300 ml. of water and 300 ml. of toluene were added followed by extraction.

The extract was washed with 300 ml. of water twice, dried over sodium sulfate, concentrated, and 500 ml. of heptane was added and the thus-precipitated crystal was filtered off. The filtrate was concentrated, passed through a column packed with silica gel using a heptane followed by concentration again. To the concentrate was added 150 ml. of 2 N hydrochloric acid and 300 ml. of THF and refluxed for two hours.

After allowing to cool, 300 ml. of toluene was added and extraction was carried out, and the extract was washed with 200 ml. of 0.5 N aqueous sodium hydroxide and with 200 ml. of water three times.

The product thus washed was dried over sodium sulfate and concentrated to give 25.5 g. of a crude product, which was then distilled to give 16.5 g. of the end product. The structure of the final product was confirmed by NMR.

(iv) Preparation of 2-(trans-4-(3,4-difluorophenyl)cyclohexyl)-1-(trans-4-n-pentylcyclohexyl)-ethene (X=F, R =n-pentyl, m=1, n=0 in formula [I'])

A 500 ml. three-necked flask containing 15.7 g. of trans-4-n-pentylcyclohexylmethyl triphenyl phosphonium bromide and 100 ml. of THF was cooled to −50° C. and 3.5 g. of potassium t-butoxide was added.

After stirring for one hour at −50° C., 50 ml. of a solution of the compound obtained in (iii) above (6.3 g.) in THF was dropwise added thereto and the temperature was gradually raised up to 0° C. with stirring over 4 hours, and 150 ml. of water and 150 ml. of toluene were added followed by extraction. The extract was washed with 200 ml. of water twice, dried over sodium sulfate and concentrated.

To the concentrate was added 150 ml. of heptane, and the crystal thus precipitated was filtered off, and the concentrated filtrate was passed through a column packed with silica gel using a heptane followed by distilling off heptane to obtain the final product (5.5 g.).

The ratio of the cis-form to the trans-form was 95:5.

(v) Preparation of trans-2-(trans-4-(3,4-difluorophenyl)cyclohexyl)-1-(trans-4-n-pentylcyclohexyl)ethene (l=5 in form of [Ib'])

A 100 ml. three-necked flask containing 5.1 g. of metachloroperbenzoic acid, 3.0 g. of potassium carbonate and 10 ml. of chloroform was cooled to 10° C., and 20 ml. of a solution of the compound obtained in (iv) above (5.5 g.) in chloroform was added thereto.

After stirring for two hours, a 10% aqueous sodium thiosulfate (30 ml.) was added and stirring was effected for 5 min. After removing the water layer, the product was washed with 30 ml. of a 0.5 N aqueous sodium hydroxide, and with 30 ml. of water three times, and dried over sodium sulfate. After concentration, the concentrate was passed through a column packed with silica gel using a heptane, and heptane was distilled off to give 5.2 g. of an oily product.

To a 100 ml. three-necked flask containing 8.4 g. of dibromotriphenylphosphorane and 30 ml. of benzene was added 15 ml. of a solution of the above-mentioned oily product (5.2 g.) in benzene and refluxed for 6 hours. After allowing to cool, the product was passed through a column packed with silica gel using a toluene and concentrated to give 7.2 g. of white crystal followed by recrystallizing from a heptane and drying to give 3.4 g. of white crystal, m.p. 151° C.

NMR spectrum of the resulting white crystal product supported the chemical structure,

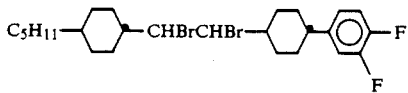

To a 100 ml. three-necked flask containing 2.2 g. of the bromo compound and 20 ml. of acetic acid was added 1.5 g. zinc, and the temperature was raised up to 45° C. After stirring for two hours, the mixture was poured into a 300 ml. beaker containing 70 ml. of water, extracted with 100 ml. of toluene, washed with 100 ml. of 0.5 N aqueous sodium hydroxide and with 50 ml. of water three times, dried over sodium sulfate and concentrated to give 2.0 g. of crude product. The crude product was recrystallized from a heptane and dried to give 0.7 g. of the final product, CN point 31° C. and NI point 136° C.

EXAMPLE 2

(X=F, m=1, and n=0 in formula [I])

The procedures of Example 1 are repeated except that appropriate phosphonium salts are used in place of trans-4-n-pentylcyclohexylmethyl triphenyl phosphonium bromide and the following compounds are obtained.

Trans-2-(trans-4-(3,4-difluorophenyl)cyclohexyl)-1-(trans-4-methylcyclohexyl)ethene (No. 2)

Trans-2-(trans-4-(3,4-difluorophenyl)cyclohexyl)-1-(trans-4-ethylcyclohexyl)ethene (No. 3)
  CN, 36.9° C. ; NI, 95.8° C.

Trans-2-(trans-4-(3,4-difluorophenyl)cyclohexyl)-1-(trans-4-n-propylcyclohexyl)ethene (No. 4)
  CN, 41.1° C. ; NI, 133.3° C.

Trans-2-(trans-4-(3,4-difluorophenyl)cyclohexyl)-1-(trans-4-n-butylcyclohexyl)ethene (No. 5)
  CN, 24.2° C. ; NI, 131.6° C.

Trans-2-(trans-4-(3,4-difluorophenyl)cyclohexyl)-1-(trans-4-n-hexylcyclohexyl)ethene (No. 6)

Trans-2-(trans-4-(3,4-difluorophenyl)cyclohexyl)-1-(trans-4-n-heptylcyclohexyl)ethene (No. 7)

Trans-2-(trans-4-(3,4-difluorophenyl)cyclohexyl)-1-(trans-4-n-octylcyclohexyl)ethene (No. 8)

EXAMPLE 3

(X=F, m=1, n=1 in formula [I])

Repeating the procedure of Example 1 except that 2-(3,4-difluorophenyl)ethyl bromide is used in place of 3,4-difluorobromobenzene and an appropriate phosphonium salt in place of trans-4-n-pentylcyclohexylmethyl triphenyl phosphonium bromide, there are produced the following compounds.

Trans-2-[trans-4-(2-(3,4-difluorophenyl)ethyl)cyclohexyl]-1-(trans-4-methylcyclohexyl)ethene (No. 9)

Trans-2-[trans-4-(2-(3,4-difluorophenyl)ethyl)cyclohexyl]-1-(trans-4-ethylcyclohexyl)ethene (No. 10)
  CN, 49.0° C. ; NI, 90.0° C.

Trans-2-[trans-4-(2-(3,4-difluorophenyl)ethyl)cyclohexyl]-1-(trans-4-n-propylcyclohexyl)ethene (No. 11)

Trans-2-[trans-4-(2-(3,4-difluorophenyl)ethyl)cyclohexyl]-1-(trans-4-n-butylcyclohexyl)ethene (No. 12)

Trans-2-[trans-4-(2-(3,4-difluorophenyl)ethyl)cyclohexyl]-1-(trans-4-n-pentylcyclohexyl)ethene (No. 13)

Trans-2-[trans-4-(2-(3,4-difluorophenyl)ethyl)cyclohexyl]-1-(trans-4-n-hexylcyclohexyl(ethene (No. 14)

Trans-2-[trans-4-(2-(3,4-difluorophenyl)ethyl)cyclohexyl]-1-(trans-4-n-heptylcyclohexyl)ethene (No. 15)

Trans-2-[trans-4-(2-(3,4-difluorophenyl)ethyl)cyclohexyl]-1-(trans-4-n-octylcyclohexyl)ethene (No. 16)

EXAMPLE 4

(X=H, m=1, n=0 in formula (I])

Repeating the procedure of Example 1 except that 4-fluorobromobenzene is used in place of 3,4-difluorobromobenzene and an appropriate phosphonium salt in place of trans-4-n-pentylcyclohexylmethyl triphenyl phosphonium bromide, there are obtained the following compounds.

Trans-2-(trans-4-(4-fluorophenyl)cyclohexyl)-1-(trans-4-methylcyclohexyl)ethene (No. 17)

Trans-2-(trans-4-fluorophenyl)cyclohexyl)-1-(trans-4-ethylcyclohexyl)ethene (No. 18)

Trans-2-(trans-4-(4-fluorophenyl)cyclohexyl)-1-(trans-4-n-propylcyclohexyl)ethene (No. 19)
CN, 64.4° C. ; NI, 167.5° C.

Trans-2-(trans-4-(4-fluorophenyl)cyclohexyl)-1-(trans- 4-n-butylcyclohexyl)ethene (No. 20)
CS, 56.4° C.; SN, 59.1° C.; NI, 163.0° C.

Trans-2-(trans-4-(4-fluorophenyl)cyclohexyl)-1-(trans-4-n-pentylcyclohexyl)ethene (No. 21)

Trans-2-(trans-4-(4-fluorophenyl)cyclohexyl)-1-(trans-4-n-hexylcyclohexyl)ethene (No. 22)

Trans-2-(trans-4-(4-fluorophenyl)cyclohexyl)-1-(trans-4-n-heptylcyclohexyl)ethene (No. 23)

Trans-2-(trans-4-(4-fluorophenyl)cyclohexyl)-1-(trans-4-n-octylcyclohexyl)ethene (No. 24)

EXAMPLE 5

(X=H, m=1, n=1 in formula [I])

Repeating the procedure of Example 1 except that 2-(4-fluorophenyl) ethyl bromide is used in place of 3,4-difluorobromobenzene and an appropriate phosphonium salt in place of trans-4-n-pentylcyclohexylmethyl triphenyl phosphonium bromide, there are produced the following compounds.

Trans-2-[trans-4-(2-(4-fluorophenyl)ethyl)cyclohexyl]-1-(trans-4-methylcyclohexyl)ethene (No. 25)

Trans-2-[trans-4-(2-(4-fluorophenyl)ethyl)cyclohexyl]-1-(trans-4-ethylcyclohexyl)ethene (No. 26)

Trans-2-[trans-4-(2-(4-fluorophenyl)ethyl)cyclohexyl]-1-(trans-4-n-propylcyclohexyl)ethene (No. 27)

Trans-2-[trans-4-(2-(4-fluorophenyl)ethyl)cyclohexyl[-1-(trans-4-n-butylcyclohexyl)ethene (No. 28)

Trans-2-[trans-4-(2-(4-fluorophenyl)ethyl)cyclohexyl]-1-(trans-4-n-pentylcyclohexyl)ethene (No. 29)

Trans-2-[trans-4-(2-(4-fluorophenyl)ethyl cyclohexyl]-1-(trans-4-n-hexylcyclohexyl)ethene (No. 30)

Trans-2-[trans-4-(2-(4-fluorophenyl)ethyl)cyclohexyl]-1-(trans-4-n-heptylcyclohexyl)ethene (No. 31)

Trans-2-[trans-4-(2-(4-fluorophenyl)ethyl)cyclohexyl]-1-(trans-4-n-octylcyclohexyl)ethene (No. 32)

EXAMPLE 6

(X=F, m=2, n=0 in formula [I])

Repeating the procedure of Example 1 except that an appropriate phosphonium salt is used in place of trans-4-n-pentylcyclohexylmethyl triphenyl phosphonium bromide, there are obtained the following compounds.

Trans-2-(trans-4-(3-,4-difluorophenyl)cyclohexyl)-1-(trans-4-(trans-4-methylcyclohexyl)cyclohexyl)ethene (No. 33)

Trans-2-(trans-4-(3,4-difluorophenyl)cyclohexyl)-1-(trans-4-(trans-4-ethylcyclohexyl)cyclohexyl)ethene (No. 34)

Trans-2-(trans-4-(3,4-difluorophenyl)cyclohexyl)-1-(trans-4-(trans-4-n-propylcyclohexyl)cyclohexyl)ethene (No. 35) CS, 70.5° C.; SN, 168.4° C.; NI>300° C.

Trans-2-(trans-4-(3,4-difluorophenyl)cyclohexyl)-1-(trans-4-(trans-4-n-butylcyclohexyl)cyclohexyl)ethene (No. 36)

Trans-2-(trans-4-(3,4-difluorophenyl)cyclohexyl)-1-(trans-4-(trans-4-n-pentylcyclohexyl)cyclohexyl)ethene (No. 37)

EXAMPLE 7

(X=F, m=2, n=1 in formula [I])

Repeating the procedure of Example 1 except that 2-(3,4-difluorophenyl)ethyl bromide is used in place of 3,4-difluorobromobenzene and an appropriate phosphonium salt in place of trans-4-n-pentylcyclohexylmethyl triphenyl phosphonium bromide, the following compounds are produced.

Trans-2-[trans-4-(2-(3,4-difluorophenyl)ethyl)cyclohexyl]-1-(trans-4-(trans-4-methylcyclohexyl)cyclohexyl)ethene (No. 38)

Trans-2-[trans-4-(2-(3,4-difluorophenyl)ethyl)cyclohexyl]-1-(trans-4-(trans-4-ethylcyclohexyl)cyclohexyl)ethene (No. 39)

Trans-2-[trans-4-(2-(3,4-difluorophenyl)ethyl)cyclohexyl]-1-(trans-4-(trans-4-n-propylcyclohexyl)cyclohexyl)ethene (No. 40)

Trans-2-[trans-4-(2-(3,4-difluorophenyl)ethyl)cyclohexyl]-1-(trans-4-(trans-4-n-butylcyclohexyl)cyclohexyl)ethene (No. 41)

Trans-2-[trans-4-(2-(3,4-difluorophenyl)ethyl)cyclohexyl]-1-(trans-4-(trans-4-n-pentylcyclohexyl)cyclohexyl)ethene (No. 42)

EXAMPLE 8

(X=H, m=2, n=0 in form [I])

Repeating the procedure of Example 1 except that 4-fluorobromobenzene is used in place of 3,4-difluorobromobenzene and an appropriate phosphonium salt in place of trans-4-n-pentylcyclohexylmethyl triphenyl phosphonium bromide, the following compounds are produced.

Trans-2-(trans-4-(4-fluorophenyl)cyclohexyl)-1-(trans-4-(trans-4-methylcyclohexyl)cyclohexyl)ethene (No. 43)

Trans-2-(trans-4-(4-fluorophenyl)cyclohexyl)-1-(trans-4-(trans-4-ethylcyclohexyl)cyclohexyl)ethene (No. 44)

Trans-2-(trans-4-(4-fluorophenyl)cyclohexyl)-1-(trans-4-(trans-4-n-propylcyclohexyl)cyclohexyl)ethene (No. 45)

Trans-2-(trans-4-(4-fluorophenyl) cyclohexyl)-1-(trans-4-(trans-4-n-butylcyclohexyl)cyclohexyl)ethene (No. 46)

Trans-2-(trans-4-(4-fluorophenyl)cyclohexyl)-1-(trans-4-(trans-4-n-pentylcyclohexyl)cyclohexyl)ethene (No. 47)

EXAMPLE 9

(X=H, m=2, n=1 in form [I])

Repeating the procedure of Example 1 except that 2-(4-fluorophenyl)ethyl bromide is used in place of 3,4difluorobromobenzene and an appropriate phosphonium salt in place of trans-4-n-pentylcyclohexylmethyl triphenyl phosphonium bromide, the following compounds are obtained.

Trans-2-[trans-4-(2-(4-fluorophenyl)ethyl)cyclohexyl]-1-(trans-4-(trans-4-methylcyclohexyl)cyclohexyl)ethene (No. 48)

Trans-2-[trans-4-(2-(4-fluorophenyl)ethyl)cyclohexyl]-1-(trans-4-(trans-4-ethylcyclohexyl)cyclohexyl)ethene (No. 49)

Trans-2-[trans-4-(2-(4-fluorophenyl)ethyl)cyclohexyl]-1-(trans-4-(trans-4-n-propylcyclohexyl)cycloyexyl)ethene (No. 50)

Trans-2-[trans-4-(2-(4-fluorophenyl)ethyl)cyclohexyl]-1-(trans-4-(trans-4-n-butylcyclohexyl)cyclohexyl)ethene (No. 51)

Trans-2-[trans-4-(2-(4-fluorophenyl)ethyl)cyclohexyl]-1-(trans-4-(trans-4-n-pentylcyclohexyl)cyclohexyl)ethene (No. 52)

EXAMPLE 10

| Structure | Amount |
|---|---|
| n-C₃H₇—[Cy]—[Ph]—CN | 30 parts by weight |
| n-C₅H₁₁—[Cy]—[Ph]—CN | 40 parts by weight |
| n-C₇H₁₅—[Cy]—[Ph]—CN | 30 parts by weight |

A liquid crystal composition A composed of the above-mentioned components has an NI point of 52.3° C., $\Delta\epsilon$ of 10.7 and $\Delta n$ of 0.119 and a viscosity of 22 cp at 20° C.

To 85 parts by weight of the liquid crystal composition A was added 15 parts by weight of the compound of Example 1 of the present invention. The resulting liquid crystal composition had an NI point of 59.1° C., $\Delta\epsilon$ of 9.7, $\Delta n$ of 0.114, and viscosity of 20.6 cp at 20° C.

COMPARATIVE EXAMPLE

The following table shows an NI point of each of compounds of the above-mentioned formulas [II], [III] and [IV] and viscosity of three liquid crystal compositions which are composed of the liquid crystal composition A as in Example 10 and 15 parts by weight of the compounds of formulas [II], [III] and [IV], respectively. The result of Example 10 is also shown.

TABLE

Comparison of NI point and viscosity ($\eta_{20}$)

| Compound | NI point | $\eta_{20}$ (CP) |
|---|---|---|
| Example 10 — C₅H₁₁—[Cy]—CH=CH—[Cy]—[Ph(F)]—F [I] | 136° C. | 20.6 |
| Comparative Example — C₅H₁₁—[Cy]—CH₂CH₂—[Cy]—[Ph(F)]—F [II] | 110° C. | 21.4 |
| C₅H₁₁—[Cy]—[Cy]—[Ph(F)]—F [III] | 125° C. | 22.1 |
| C₅H₁₁—[Cy]—CH₂CH₂—[Ph]—[Ph(F)]—F [IV] | 96° C. | 25.2 |

As is clear from the table above, the compound of the present invention exhibits the highest NI point and the lowest viscosity as compared with the analogues.

What is claimed is:

1. A dicyclohexylethylene derivative of the formula,

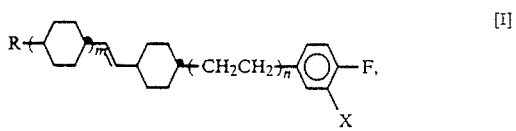

[I]

where R is a straight chain alkyl group of 1 to 8 carbon atoms, X is a hydrogen or fluorine atom, m is 1 or 2, n is 0 or 1, and indicates that a substituent at the 1-position of the cyclohexane ring and a substituent at the 4-position thereof ar at a trans configuration.

2. The dicyclohexylethylene derivative according to claim 1, having the formula,

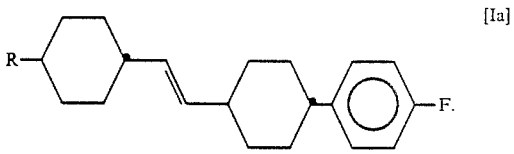

[Ia]

3. The dicyclohexylethylene derivative according to claim 1, having the formula,

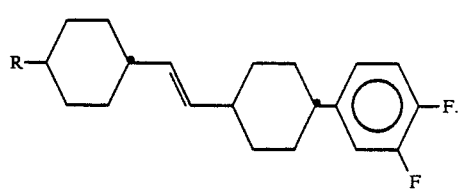
[Ib]

4. The dicyclohexylethylene derivative according to claim 1, having the formula,

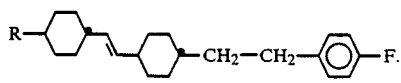
[Ic]

5. The dicyclohexylethylene derivative according to claim 1, having the formula,

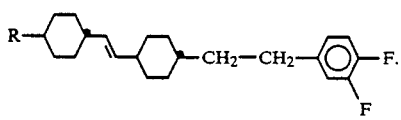
[Id]

6. The dicyclohexylethylene derivative according to claim 1, having the formula,

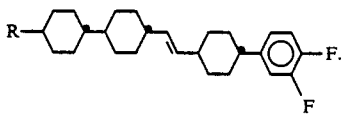
[Ie]

7. The dicyclohexylethylene derivative according to claim 1, having the formula,

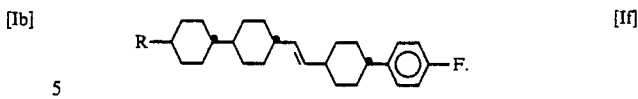
[If]

8. The dicyclohexylethylene derivative according to claim 1, having the formula,

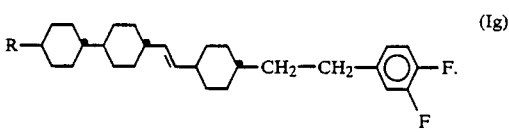
(Ig)

9. The dicyclohexylethylene derivative according to claim 1, having the formula,

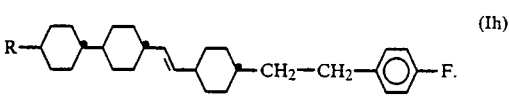
(Ih)

10. A liquid crystal composition which comprises at least one dicyclohexylethylene derivative of the formula,

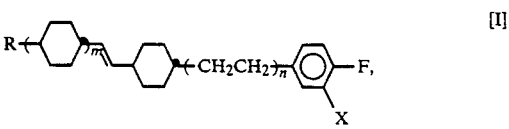
[I]

where R is a straight chain alkyl group of 1 to 8 carbon atoms, X is a hydrogen or fluorine atom, m is 1 or 2, n is 0 or 1, and indicates that a substituent at the 1-position of the cyclohexane ring and a substituent at the 4-position thereof are at a trans configuration.

* * * * *